United States Patent
Ra et al.

(10) Patent No.: US 10,815,459 B2
(45) Date of Patent: Oct. 27, 2020

(54) METHOD FOR MANUFACTURING STEM CELL HAVING APPROPRIATE SIZE FOR INTRAVASCULAR ADMINISTRATION

(71) Applicants: K-STEMCELL CO., LTD., Seoul (KR); Jeong Chan Ra, Gyeonggi-do (KR)

(72) Inventors: Jeong Chan Ra, Gyeonggi-do (KR); Sung Keun Kang, Seoul (KR); Il Seob Shin, Seoul (KR)

(73) Assignees: Jeong Chan Ra, Gyeonggi-do (KR); K-STEMCELL CO., LTD., Seoul (KR)

( * ) Notice: Subject to any disclaimer, the term of this patent is extended or adjusted under 35 U.S.C. 154(b) by 0 days.

(21) Appl. No.: 14/395,170

(22) PCT Filed: Apr. 17, 2013

(86) PCT No.: PCT/KR2013/003251
§ 371 (c)(1),
(2) Date: Oct. 17, 2014

(87) PCT Pub. No.: WO2013/157850
PCT Pub. Date: Oct. 24, 2013

(65) Prior Publication Data
US 2015/0072421 A1    Mar. 12, 2015

(30) Foreign Application Priority Data

Apr. 18, 2012  (KR) .................. 10-2012-0040488

(51) Int. Cl.
*C12N 5/0775*    (2010.01)
(52) U.S. Cl.
CPC ........ *C12N 5/0667* (2013.01); *C12N 2500/14* (2013.01); *C12N 2500/32* (2013.01); *C12N 2500/38* (2013.01); *C12N 2501/11* (2013.01); *C12N 2501/115* (2013.01); *C12N 2501/33* (2013.01); *C12N 2501/39* (2013.01)
(58) Field of Classification Search
None
See application file for complete search history.

(56) References Cited

U.S. PATENT DOCUMENTS

| | | |
|---|---|---|
| 6,103,530 A | 8/2000 | Carpenter |
| 2007/0082394 A1 | 4/2007 | Moscatello |
| 2007/0110729 A1* | 5/2007 | Kang .................. C12N 5/0667 424/93.7 |
| 2009/0124007 A1 | 5/2009 | Cho |
| 2009/0233360 A1 | 9/2009 | Baghbaderani et al. |
| 2011/0312091 A1 | 12/2011 | Zhao et al. |
| 2012/0122816 A1* | 5/2012 | Gjorstrup ............. A01N 1/0226 514/63 |
| 2012/0276044 A1* | 11/2012 | Ra ........................ C12N 5/0667 424/85.1 |

FOREIGN PATENT DOCUMENTS

| | | |
|---|---|---|
| EP | 2 594 636 A2 | 5/2013 |
| EP | 2 811 015 A1 | 12/2014 |
| EP | 2 837 682 A1 | 2/2015 |
| EP | 2 865 749 A1 | 4/2015 |
| JP | 2008-212022 A | 9/2008 |
| JP | 2010-537663 A | 12/2010 |
| KR | 10-2008-0075959 A | 8/2008 |
| KR | 10-2012-0057784 A | 6/2012 |
| WO | 2009/061024 A1 | 5/2009 |
| WO | 2012/012570 A2 | 1/2012 |

OTHER PUBLICATIONS

Solchaga et al., FGF-2 Enhances the Mitotic and Chondrogenic Potentials of Human Adult bone Marrow-Derived Mesenchymal Stem Cells, Journal of Cellular Physiology, vol. 203:398-409 (2005).*
Jung et al., Ex Vivo Expansion of Huyman Mesenchymaml Stem Cells in Defined Serum-Free Media, Stem Cells International, vol. 2012, 21 pages.*
Furlani et al., "Is the intravascular administration of mesenchymal stem cells safe? Mesenchymal stem cells and intravital microscopy", Microvasular Research, vol. 77, pp. 370-376, (2009).
Extended European search report for European application No. 13 77 7949, nine pages, completed Nov. 24, 2015.
Japanese Office Action for Japanese application No. 2015-506897, seven pages, dated Nov. 30, 2015.
Ra et al., "Stem cell treatment for patients with autoimmune disease by systemic infusion of culture-expanded autologous adipose tissue derived mesenchymal stem cells", Journal of Translational Medicine, vol. 9, p. 181 (11 pages), (2011).
Ra et al., "Safety of Intravenous Infusion of Human Adipose Tissue-Derived Mesenchymal Stem Cells in Animals and Humans", Stem Cells and Development, vol. 20, No. 8, pp. 1297-1308, (2011).

\* cited by examiner

*Primary Examiner* — Scott Long
*Assistant Examiner* — Evelyn Y Pyla
(74) *Attorney, Agent, or Firm* — Vorys, Sater, Seymour & Pease LLP; Mih Suhn Koh

(57) ABSTRACT

The present invention relates to a method for preparing stem cells having a size suitable for intravascular administration, and preferably to a method for preparing stem cells with a diameter ranging from 11-16 μm. Additionally, the present invention relates to media composition for preparing stem cells having a size suitable for intravascular administration. According to the present invention, stem cells having a size suitable for intravascular administration can be prepared such that stem cells administered into a vein can stably reach a target tissue, and thus can more efficiently increase efficacy displaying activity, thereby innovatively enhancing the efficacy of cell therapy using stem cells.

3 Claims, 2 Drawing Sheets

METHOD FOR MANUFACTURING STEM CELL HAVING APPROPRIATE SIZE FOR INTRAVASCULAR ADMINISTRATION

TECHNICAL FIELD

The present invention relates to a method for preparing stem cells having a size suitable for intravascular administration, and more particularly to a method for preparing stem cells having a diameter of 1-16 μm, which is suitable for intravascular administration.

BACKGROUND ART

Stem cells refer to cells having not only self-replicating ability but also the ability to differentiate into at least two types of cells, and can be divided into totipotent stem cells, pluripotent stem cells, and multipotent stem cells. Totipotent stem cells are cells having totipotent properties capable of developing into one perfect individual, and these properties are possessed by cells up to the 8-cell stage after the fertilization of an oocyte and a sperm. When these cells are isolated and transplanted into the uterus, they can develop into one perfect individual. Pluripotent stem cells, which are cells capable of developing into various cells and tissues derived from the ectodermal, mesodermal and endodermal layers, are derived from an inner cell mass located inside of blastocysts generated 4-5 days after fertilization. These cells are called "embryonic stem cells" and can differentiate into various other tissue cells but not form new living organisms. Multipotent stem cells, which are stem cells capable of differentiating into only cells specific to tissues and organs containing these cells, are involved not only in the growth and development of various tissues and organs in the fetal, neonatal and adult periods but also in the maintenance of homeostasis of adult tissue and the function of inducing regeneration upon tissue damage. Tissue-specific multipotent cells are collectively called "adult stem cells".

Adult stem cells are obtained by taking cells from various human organs and developing the cells into stem cells and are characterized in that they differentiate into only specific tissues. However, recently, experiments for differentiating adult stem cells into various tissues, including liver cells, were dramatically successful, which comes into spotlight. In particular, efforts have been made in the field of regenerative medicine for regenerating biological tissues and organs and recovering their functions that were lost due to illness or accident and the like by using cells. Methods which are frequently used in this field of regenerative medicine comprise the steps of: collecting stem cells, blood-derived mononuclear cells or marrow-derived mononuclear cells from a patient; inducing the proliferation and/or differentiation of the cells by tube culture; and introducing the selected undifferentiated (stem cells and/or progenitor cells) and/or differentiated cells into the patient's body by transplantation. Accordingly, existing classical methods for treating diseases by medication or surgery are expected to be replaced with cell/tissue replacement therapy which replaces a damage cell, tissue or organ with healthy one, and thus the utility of stem cells will further increase.

Thus, the various functions of stem cells are currently being studied. Particularly, since cell therapy technology using mesenchymal stem cells started to receive attention, technology for improving mesenchymal stem cells so as to be suitable for therapeutic purposes have been developed (WO 2006/019357, Korean Patent No. 0795708, and Korean Patent No. 0818214).

However, technology related to a method for preparing stem cells suitable for intravascular administration has not yet been sufficiently studied.

Accordingly, the present inventors have found that, when stem cells are cultured in a medium containing a basal medium and at least two components selected from the group consisting of N-acetyl-L-cysteine (NAC), insulin or insulin-like factor, hydrocortisone, basic fibroblast growth factor (bFGF), and antioxidant, stem cells having a size suitable for intracellular administration can be prepared, thereby completing the present invention.

DISCLOSURE OF INVENTION

Technical Problem

It is an object of the present invention to provide a method for preparing stem cells having a size suitable for intravascular administration.

Another object of the present invention is to provide a medium composition for preparing stem cells having a size suitable for intravascular administration.

Technical Solution

To achieve the above objects, the present invention provides a method for preparing stem cells having a size suitable for intravascular administration, the method comprising the step of culturing stem cells in a medium containing a basal medium; and at least two components selected from the group consisting of N-acetyl-L-cysteine (NAC), insulin or insulin-like factor, hydrocortisone, basic fibroblast growth factor (bFGF), and antioxidant.

The present invention also provides a medium composition for preparing stem cells having a size suitable for intravascular administration, the medium composition containing a basal medium; and at least two components selected from the group consisting of N-acetyl-L-cysteine (NAC), insulin or insulin-like factor, hydrocortisone, basic fibroblast growth factor (bFGF), and antioxidant.

BEST MODE FOR CARRYING OUT THE INVENTION

Figure 1:
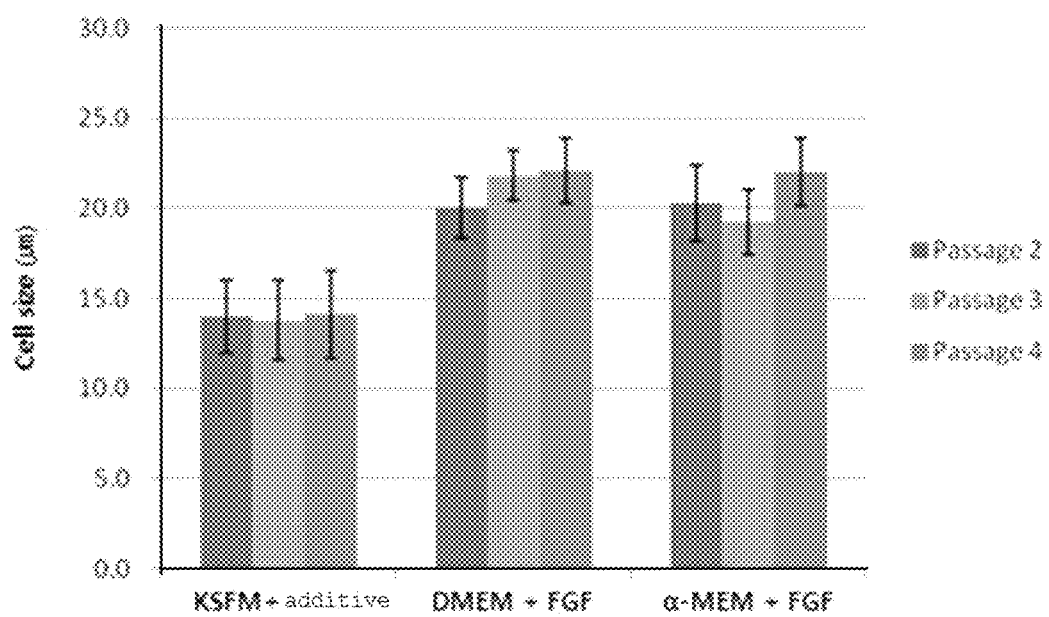
FIG. 1 is a graphic diagram showing the size of adipose-derived mesenchymal stem cells according to medium and passage number.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

As used herein, the term "stem cells" refer to cells having not only self-replicating ability but also the ability to differentiate into at least two types of cells. "Adult stem cells" refer to stem cells that appear either in the stage in which each organ of an embryo is formed after the developmental process or in the adult stage.

As used herein, the term "mesenchymal stem cells" refers to undifferentiated stem cells that are isolated from human or mammalian tissue and may be derived from various tissues. Particularly, the mesenchymal stem cells may be umbilical cord-derived mesenchymal stem cells, umbilical cord blood-derived mesenchymal stem cells, bone marrow-derived mesenchymal stem cells, adipose-derived mesenchymal stem cells, muscle-derived mesenchymal stem cells, nerve-derived mesenchymal stem cells, skin-derived mesenchymal stem cells, amnion-derived mesenchymal stem cells, or placenta-derived mesenchymal stem cells. Technology for isolating stem cells from each tissue is already known in the art.

As used herein, "adipose tissue-derived mesenchymal stem cells" are undifferentiated adult stem cells isolated from adipose tissue and are also referred to herein as "adipose-derived adult stem cells", "adipose stem cells", or "adipose-derived stem cells". These cells can be obtained according to any conventional method known in the art. A method for isolating adipose tissue-derived mesenchymal stem cells may be, for example, as follows. That is, adipose-derived mesenchymal stem cells can be isolated by culturing an adipose-containing suspension (in physiological saline) obtained by liposuction, and then either collecting a stem cell layer, attached to a culture container such as a flask, by trypsin treatment, or directly collecting those suspended in a small amount of physiological saline by rubbing with a scraper.

In the present invention, "stem cells having a size suitable for intravascular administration" refers to stem cells that have a diameter of preferably 11-16 μm, which is smaller than the diameter of veins or capillary vessels, such that the stem cells, when administered intravascularally, can easily migrate to their target tissue without interfering with blood flow or circulation and can exhibit their activity in the target tissue.

Stem cells can be administered into the body by various routes, for example, intravenously, intra-arterially or intra-peritoneally. Among such administration routes, intravenous administration is preferred, because it enables a disease to be treated in a convenient and safe manner without surgical operation. In order for intravenously administered stem cells to securely reach the target site and to exhibit a desired therapeutic effect, various requirements should be satisfied. First, stem cells should have a size suitable for intravascular administration such that these stem cells, when administered intravascularly, neither reduce blood flow velocity nor form thrombi. The degree of proliferation of mesenchymal stem cells that can be derived from various tissues differs between patients and varies depending on their origin, culture condition or method, and the size thereof also varies from about 10 to 300 μm in diameter. However, human post-capillary venules have a diameter of about 10-50 μm, arterioles have a diameter of 8-30 μm (Schmidt G T, 1989), and capillary vessels have a diameter of about 8 μm (Schmidt G T, 1989; Chien, 1975; John Ross, 1991; Herbert et al., 1989; Arthur and Guyton, 1997; Renkin, 1989; Gaehtgens, 1980; Row 1979), which are smaller than the diameter of general mesenchymal stem cells. Thus, when mesenchymal stem cells having a relatively large size are administered intravascularly, they can influence intravascular activity. Specifically, they can reduce blood flow velocity and also interfere with blood circulation to cause blood flow stoppage, thrombus formation and vascular obstruction, even leading to death. In connection with this, it was reported that, when mesenchymal stem cells having a diameter of about 16-53 μm administered intravenously to mice, blood flow velocity was reduced and the induction of myocardial infarction and thrombus formation was observed (D. Furlani et al. Microvasular Research 77 (2009) 370-376). Thus, it is important to administer stem cells having a suitable size by an intracellular route. Moreover, stem cells should not be disrupted or aggregated before intravascular administration, and should securely reach their target site as single cells without disruption or aggregation after intravascular administration. In addition, stem cells should be administered at a certain concentration or higher concentration such that they exhibit a desired therapeutic effect after they reached the target site. In view of several requirements as described above, the present invention is intended to provide stem cells that have a size suitable for intravascular administration so as to securely exhibit a therapeutic effect without reducing blood flow velocity or forming thrombi after intravascular administration.

In one aspect, the present invention is directed to a method for preparing stem cells having a size suitable for intravascular administration, the method comprising the step of culturing stem cells in a medium containing a basal medium; and at least two components selected from the group consisting of N-acetyl-L-cysteine (NAC), insulin or insulin-like factor, hydrocortisone, basic fibroblast growth factor (bFGF), and antioxidant.

The basal medium used in the present invention refers to a typical medium having a simple composition known as being suitable for the culture of stem cells. Examples of the basal medium generally used to culture the stem cells include MEM (Minimal Essential Medium), DMEM (Dulbecco modified Eagle Medium), RPMI (Roswell Park Memorial Institute Medium), and K-SFM (Keratinocyte Serum Free Medium). As the basal medium used in the present invention, any mediums can be used without any limitation as long as they are used in the art. Preferably, the basal medium may be selected from the group consisting of M199/F12(mixture)(GIBCO), MEM-alpha medium (GIBCO), low-concentration glucose-containing DMEM medium (Welgene), MCDB 131 medium (Welgene), IMEM medium (GIBCO), K-SFM, DMEM/F12 medium, PCM medium, and MSC expansion medium (Chemicon). Particularly, among them, K-SFM may be preferably used.

A basal medium that is used to obtain the cultured mesenchymal stem cells may be supplemented with additives in the art, which promote the proliferation of mesenchymal stem cells in an undifferentiated state while inhibiting the differentiation thereof. Also, the medium may contain a neutral buffer (such as phosphate and/or high-concentration bicarbonate) in isotonic solution, and a protein nutrient (e.g., serum such as FBS, FCS (fetal calf serum) or horse serum, serum replacement, albumin, or essential or non-essential amino acid such as glutamine or L-glutamine). Furthermore, it may contain lipids (fatty acids, cholesterol, an HDL or LDL extract of serum) and other ingredients found in most stock media of this kind (such as insulin or transferrin, nucleosides or nucleotides, pyruvate, a sugar source such as glucose, selenium in any ionized form or salt, a glucocorticoid such as hydrocortisone and/or a reducing agent such as β-mercaptoethanol).

Also, for the purpose of preventing cells from adhering to each other, adhering to a container wall, or forming too large clusters, the medium may advantageously contain an anti-clumping agent, such as one sold by Invitrogen (Cat #0010057AE).

Among them, one or more of the following additional additives may advantageously be used:
 stem cell factor (SCF, Steel factor), other ligands or antibodies that dimerize c-kit, and other activators of the same signaling pathway ligands for other tyrosine kinase related receptors, such as the receptor for platelet-derived growth factor (PDGF), macrophage colony-stimulating factor, Flt-3 ligand and vascular endothelial growth factor (VEGF)

factors that elevate cyclic AMP levels, such as forskolin factors that induce gp130 such as LIF or Oncostatin-M hematopoietic growth factors such as thrombopoietin (TPO)

transforming growth factors such as TGFβ1 neurotrophins such as CNTF antibiotics such as gentamicin, penicillin or streptomycin.

The medium that is used in the present invention may contain, in addition to the basal medium, at least two components selected from the group consisting of N-acetyl-L-cysteine (NAC), insulin or insulin-like factor, hydrocortisone, basic fibroblast growth factor (bFGF), and antioxidant.

Specifically, the medium may contain insulin-like factor as insulin replacement, which functions to promote cell growth by enhancing glucose metabolism and protein metabolism. Particularly, recombinant IGF-1 (insulin-like growth factor-1) is preferably used. The preferred content of insulin-like factor is 10-50 ng/ml. If the content of insulin-like factor is less than 10 ng/ml, apoptosis will occur, and if the content is more than 50 ng/ml, it will increase the cytotoxicity and cost of the medium.

The medium may contain basic fibroblast growth factor (bFGF) that can induce various types of cell proliferation in vivo. Preferably, recombinant bFGF protein is used. The preferred content of bFGF is 1-100 ng/ml.

Examples of an antioxidant that may be used in the present invention include selenium, ascorbic acid, vitamin E, catechin, lycopene, β-carotene, coenzyme Q-10, EPA (eicosapentaenoic acid), DHA (docosahexanoic acid) and the like. Preferably, selenium may be used. In an example of the present invention, selenium was used as an antioxidant. The content of selenium in the medium is preferably 0.5-10 ng/ml. If the content of selenium is less than 0.5 ng/ml, the medium will be sensitive to oxygen toxicity, and if the content is more than 10 ng/ml, it will cause severe cytotoxicity.

The medium that is used in the present invention may additionally contain a component selected from the group consisting of FBS (fetal bovine serum), calcium and EGF. Epidermal growth factor (EGF) can induce various types of cell proliferation in vivo, and recombinant EGF protein is preferably used. The preferred content of epidermal growth factor is 10-50 ng/ml. If the content of epidermal growth factor in the medium is less than 10 ng/ml, it will have no particular effect, and if the content is more than 50 ng/ml, it will be toxic to cells.

Stem cells cultured in the medium according to the present invention preferably have a diameter of 11-16 μm, and thus are suitable for intravascular administration.

Thus, in another aspect, the present invention is directed to a medium composition for preparing stem cells having a size suitable for intravascular administration, the medium composition containing a basal medium; and at least two components selected from the group consisting of N-acetyl-L-cysteine (NAC), insulin or insulin-like factor, hydrocortisone, basic fibroblast growth factor (bFGF), and antioxidant.

In an example of the present invention, adipose-derived mesenchymal stem cells were cultured in the medium of the present invention. Adipose-derived mesenchymal stem cells can be obtained in the following manner. First, human adipose tissue obtained from the abdomen by liposuction or the like is isolated and washed with PBS, after which the tissue is cut finely and degraded using DMEM medium containing collagenase. The degraded tissue is washed with PBS and centrifuged at 1000 rpm for 5 minutes. The supernatant is removed, and the pellet remaining at the bottom is washed with PBS, and then centrifuged at 1000 rpm for 5 minutes. The resulting cells are filtered through a 100-mesh filter to remove the debris, and then washed with PBS. The cells are cultured overnight in DMEM medium (10% FBS, 2 mM NAC, 0.2 mM ascorbic acid), and then the cells that did not adhere to the bottom of the culture container were washed out with PBS, and the cells are subcultured while the medium was replaced with K-SFM medium containing NAC, ascorbic acid, calcium, rEGF, insulin and hydrocortisone at 2-day intervals, thereby obtaining adipose-derived mesenchymal stem cells. In addition to this method, any method known in the art may also be used to obtain mesenchymal stem cells.

The preparation method of the present invention may further comprise the step of treating the stem cells, cultured in the medium of the present invention, with trypsin. When the cultured stem cells are treated with trypsin, stem cells in the form of single cells can be obtained. Herein, trypsin functions to inhibit intercellular aggregation such that the cells are maintained as single cells. Any substance capable of inhibiting intercellular aggregation may also be used in place of trypsin.

The preparation method of the present invention may further comprise a step of suspending the stem cells, cultured in the medium of the present invention, in an aspirin-containing solution. When the cultured stem cells are suspended in an aspirin-containing solution, the stem cells can effectively be prevented from being disrupted or aggregated during transport or storage. Thus, the stem cells that are used for intravascular administration may be used after they are suspended in an aspirin-containing physiological saline. The aspirin-containing solution refers to a solution containing an aspirin compound. The solvent of the solution may be physiological saline. In addition to physiological saline, any base, such as Hartman-D solution or PBS (phosphate buffered saline), which is generally used in the art, may be used without limitation. As the aspirin, not only a commercially available aspirin formulation, but also an aspirin-like compound may be used. The amount of aspirin added is preferably 0.0001-0.01 mg/ml. If the amount of aspirin added is larger than the upper limit of the above range, cell viability can decrease, and if the amount is smaller than the lower limit of the above range, the effect of inhibiting cell aggregation can be insufficient.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Isolation of Human Adipose Tissue-Derived Mesenchymal Stem Cells

Adipose tissue isolated from abdominal tissue by liposuction was washed with PBS and cut finely, after which the tissue was digested in DMEM media supplemented with collagenase type 1 (1 mg/ml) at 37 r for 2 hours. The collagenase-treated tissue was washed with PBS and centrifuged at 1000 rpm for 5 minutes. The supernatant was removed, and the pellet was washed with PBS and then centrifuged at 1000 rpm for 5 minutes. The resulting cells were filtered through a 100-mesh filter to remove debris, after which the cells were washed with PBS and cultured overnight in DMEM medium containing 10% FBS, 2 mM NAC (N-acetyl-L-cysteine) and 0.2 mM ascorbic acid.

Then, non-adherent cells were removed by washing with PBS, and the remaining cells were cultured for 3 passages while the medium was replaced with K-SFM (keratinocyte serum free medium) containing 5% FBS, 2 mM NAC, 0.2 mM ascorbic acid, 0.09 mM calcium, 5 ng/ml rEGF, 5 ng/ml insulin, 10 ng bFGF and 74 ng/ml hydrocortisone and 1 ng/ml selenium) at 2-day intervals, thereby isolating adipose-derived mesenchymal stem cells.

The adipose-derived mesenchymal stem cells obtained by culture for 3 passages in Example 1 were seeded in each of the following media and were cultured for 5 days. At 5 days of culture, the size and characteristics of the cells were measured.

Medium Composition
1) KSFM+additive: K-SFM+FBS+NAC+ascorbic acid+calcium+rEGF+insulin+bFGF+hydrocortisone+selenium;
2) DMEM+FGF: DMEM (low-glucose)+10% FBS+5 ng/ml FGF;
3) α-MEM+FGF: α-MEM+10% FBS+5 ng/ml FGF.

TABLE 1

Cell size (μm) according to medium composition

|  | Passage 2 | Passage 3 | Passage 4 |
| --- | --- | --- | --- |
| KSFM + additive | 14 ± 2.0 | 13.8 ± 2.2 | 14.1 ± 2.4 |
| DMEM + FGF | 20 ± 1.7 | 21.8 ± 1.4 | 22.1 ± 1.8 |
| α-MEM + FGF | 20.3 ± 2.1 | 19.2 ± 1.8 | 22.0 ± 1.9 |

The cell size of the cells of the 'KSFM+additive' culture group was the smallest, and the change in the cell size of the group cultured using α-MEM as the basal medium was greater than that of the DEME group. The cells of the 'KSFM+additive' group maintained a size of 11-16 μm, whereas other medium groups showed a cell size larger than 20 μm as the number of passages increased (see FIG. 1).

The characteristics of the passage-4 adipose-derived mesenchymal stem cells obtained using the above-described culture media were analyzed by FACS.

TABLE 2

|  | KSFM + additive | DMEM + FGF | α-MEM + FGF |
| --- | --- | --- | --- |
| CD 29 | 99.0% | 99.4% | 99.9% |
| CD 90 | 99.7% | 99.6% | 99.6% |
| CD 31 | 0.1% | 4.2% | 0.5% |
| CD 34 | 0.0% | 2.3% | 0.2% |
| CD 45 | 0.1% | 4.2% | 2.1% |

Figure 2:
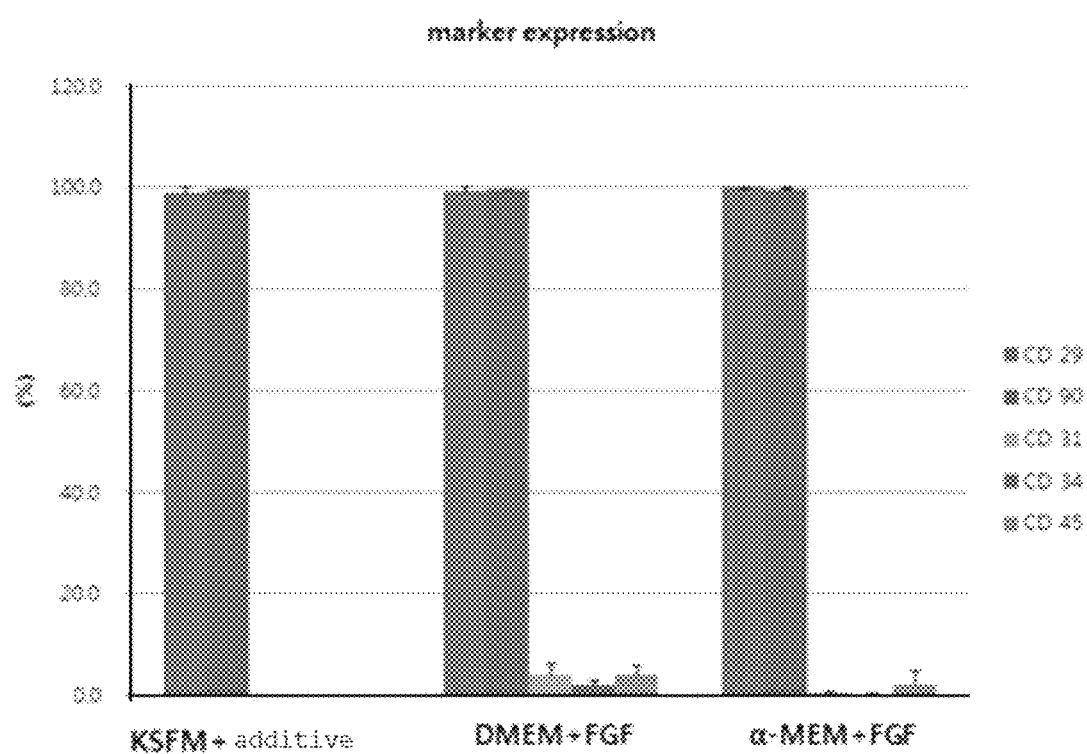
FIG. 2 is a graphic diagram showing the marker expression of adipose-derived mesenchymal stem cells according to medium.

The characteristics of the adipose-derived mesenchymal stem cells obtained using the above-described media were analyzed, and as a result, it was shown that the media had no effect on the expression of positive markers of the stem cells, but the expression level of negative markers was slightly higher in the cells of the DMEM+FGF medium group than in the cells of the 'KSFM+additive' medium group (see FIG. 2).

The stem cells isolated in Example 1 were observed by SEM (scanning electron microscopy), and as a result, it could be seen that the stem cells mostly had a diameter of about 11-16 μm and that an aggregate of the cells was not formed.

Example 2: Investigation of Medium Components for Preparation of Small-Size Stem Cells Media free of each of FBS, NAC, ascorbic acid, calcium, rEGF, 5 ng/ml insulin, bFGF, hydrocortisone and selenium, which are active ingredients added to the K-SFM medium used in Example 1, were prepared, and adipose-derived stem cells were cultured in the 'KSFM+additive' medium group and the media free of each of the active ingredients. After the cells were cultured in each of the media for 3 passages, the cells were treated with trypsin, and then the diameter of the cells was measured with a confocal microscope. As a result, it could be seen that the size of the adipose-derived stem cells cultured in the selenium-containing medium was 11.6-16.5 μm, but the size of the stem cells cultured in the selenium-free medium was 18.1-23.9 μm.

INDUSTRIAL APPLICABILITY

According to the present invention, stem cells having a diameter of 11-16 μm can be prepared, which easily migrate to their target tissue and have high stability. Thus, the effect of intravascular administration of the stem cells on cell therapy can be significantly increased.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of preparing stem cells having a size of 11-16 μm in diameter suitable for intravascular administration, comprising:
    (a) culturing isolated adipose tissue cells in a K-SFM (Keratinocyte Serum Free medium) containing basic fibroblast growth factor (bFGF), N-acetyl-L-cysteine (NAC), insulin or insulin-like factor, hydrocortisone, FBS (fetal bovine serum), calcium, and EGF (epidermal growth factor) to provide isolated stem cells;
    (b) culturing the isolated stem cells in a K-SFM containing N-acetyl-L-cysteine (NAC), insulin or insulin-like factor, hydrocortisone, basic fibroblast growth factor (bFGF), about 5% FBS (fetal bovine serum), calcium, EGF (epidermal growth factor) and about 1 ng/ml of selenium for 5 days to produce cultured stem cells having a diameter of 11-16 μm;
    (c) treating the cultured stem cells with trypsin; and
    (d) suspending the cultured stem cells in a solution containing aspirin for intravascular administration.

2. The method of claim 1, wherein the stem cells are adult stem cells.

3. The method of claim 2, wherein the stem cells are adipose tissue-derived mesenchymal stem cells.

* * * * *